(12) United States Patent
Warlick

(10) Patent No.: US 11,389,371 B2
(45) Date of Patent: Jul. 19, 2022

(54) ACOUSTIC SHOCK WAVE THERAPEUTIC METHODS

(71) Applicant: John F. Warlick, Woodstock, GA (US)

(72) Inventor: John F. Warlick, Woodstock, GA (US)

(73) Assignee: Softwave Tissue Regeneration Technologies, LLC, Woodstock, GA (US)

( * ) Notice: Subject to any disclaimer, the term of this patent is extended or adjusted under 35 U.S.C. 154(b) by 606 days.

(21) Appl. No.: 15/984,505

(22) Filed: May 21, 2018

(65) Prior Publication Data

US 2019/0350803 A1    Nov. 21, 2019

(51) Int. Cl.
*A61H 23/00*    (2006.01)
*A61B 8/00*    (2006.01)
(Continued)

(52) U.S. Cl.
CPC .......... *A61H 23/008* (2013.01); *A61B 8/085* (2013.01); *A61B 8/13* (2013.01); *G10K 15/043* (2013.01); *A61B 2090/378* (2016.02); *A61H 2201/0153* (2013.01); *A61H 2201/1654* (2013.01); *A61H 2201/50* (2013.01); *A61H 2205/087* (2013.01)

(58) Field of Classification Search
CPC .................. A61H 23/00; A61H 23/008; A61H 2205/087; A61B 17/22004; A61B 8/085; A61B 8/13; A61B 2090/378; G10K 15/043

See application file for complete search history.

(56) References Cited

U.S. PATENT DOCUMENTS

| 3,951,140 A | 4/1976 | Eggleton et al. |
| 4,539,989 A | 9/1985 | Forssmann et al. |

(Continued)

FOREIGN PATENT DOCUMENTS

| EP | 0243947 | 4/1987 |
| EP | 0324711 | 1/1989 |

(Continued)

OTHER PUBLICATIONS

Petenusci Haddad, "Stimulation of prepubertal, pubertal and adult rat restis with low-intensity pulsed ultrasound", 1994.*

(Continued)

*Primary Examiner* — Tu A Vo
(74) *Attorney, Agent, or Firm* — David L. King

(57) ABSTRACT

A method of modulating glandular secretions by administering acoustic shock waves to a gland, includes the steps of activating acoustic shock waves of an acoustic shock wave generator to emit acoustic shock waves and subjecting the gland to acoustic shock waves stimulating the gland to have a modulated response. The modulated response is one of an adjustment in hormonal release which increases low level output, decreases high level output or stabilizes erratic output. The emitted acoustic shock waves are focused or unfocused low energy acoustic shock waves. The gland underlies the patient's skin. The shock wave generator is acoustically coupled to the patient's skin using a coupling gel or liquid. The gland is one of a testicle, ovary, pituitary gland, adrenal gland, thyroid gland, thymus, pineal gland, parathyroid, or hypothalamus. The method can be repeated one or more times.

14 Claims, 12 Drawing Sheets

(51) Int. Cl.

| | |
|---|---|
| *G10K 15/04* | (2006.01) |
| *A61B 8/13* | (2006.01) |
| *A61B 8/08* | (2006.01) |
| *A61B 90/00* | (2016.01) |

(56) References Cited

U.S. PATENT DOCUMENTS

| | | | |
|---|---|---|---|
| 4,807,627 | A | 2/1989 | Eisenmenger |
| 4,868,161 | A | 9/1989 | Roberts |
| 4,905,671 | A | 3/1990 | Senge et al. |
| 5,119,801 | A | 6/1992 | Elzenhoefer et al. |
| 5,160,336 | A | 11/1992 | Favre |
| 5,173,295 | A | 12/1992 | Wehling |
| 5,174,280 | A | 12/1992 | Gruenwald et al. |
| 5,178,135 | A | 1/1993 | Uchiyama et al. |
| 5,222,484 | A | 6/1993 | Krauss et al. |
| 5,284,143 | A | 2/1994 | Rattner |
| 5,314,457 | A | 5/1994 | Jeutter et al. |
| 5,316,000 | A | 5/1994 | Chapelon et al. |
| 5,419,335 | A | 5/1995 | Hartmann |
| 5,458,130 | A | 10/1995 | Kaufman et al. |
| 5,545,124 | A | 8/1996 | Krause et al. |
| 5,595,178 | A | 1/1997 | Voss et al. |
| 5,690,926 | A | 1/1997 | Hogan |
| 5,670,372 | A | 9/1997 | Hogan |
| 6,036,661 | A | 3/2000 | Schwarze et al. |
| 6,066,123 | A * | 5/2000 | Li .................. A61K 9/0009 |
| | | | 424/450 |
| 6,068,596 | A | 5/2000 | Weth et al. |
| 6,113,560 | A | 9/2000 | Simnacher |
| 6,186,963 | B1 | 2/2001 | Schwarze et al. |
| 6,190,336 | B1 | 2/2001 | Duarte et al. |
| 6,217,531 | B1 | 4/2001 | Reitmajer |
| 6,221,021 | B1 | 4/2001 | Redano |
| 6,368,292 | B1 | 4/2002 | Ogden et al. |
| 6,390,995 | B1 | 5/2002 | Ogden et al. |
| 6,413,230 | B1 | 7/2002 | Haupt et al. |
| 6,544,987 | B2 | 4/2003 | Guo et al. |
| 6,650,935 | B1 | 11/2003 | Watmough |
| 6,723,534 | B2 | 4/2004 | Lin |
| 6,879,713 | B1 | 4/2005 | Keefe |
| 6,881,409 | B2 | 4/2005 | Gold |
| 6,884,578 | B2 | 4/2005 | Warrington et al. |
| 7,470,240 | B2 | 12/2008 | Schultheiss et al. |
| 7,485,101 | B1 * | 2/2009 | Faragalla .......... A61B 17/22004 |
| | | | 600/437 |
| 7,507,213 | B2 | 3/2009 | Schultheiss et al. |
| 7,544,171 | B2 | 6/2009 | Schaden et al. |
| 7,841,995 | B2 | 11/2010 | Schultheiss et al. |
| 7,883,482 | B2 | 2/2011 | Schultheiss et al. |
| 7,905,845 | B2 | 3/2011 | Warlick et al. |
| 7,988,648 | B2 | 8/2011 | Warlick et al. |
| 8,257,282 | B2 | 9/2012 | Uebelacker et al. |
| 8,298,162 | B2 | 10/2012 | Del Giglio |
| 8,535,249 | B2 | 9/2013 | Uebelacker et al. |
| 9,506,035 | B2 | 11/2016 | Williams et al. |
| 9,636,516 | B2 | 5/2017 | Schwartz |
| 9,713,731 | B2 | 7/2017 | Slayton et al. |
| 2002/0002345 | A1 | 1/2002 | Marlinghaus |
| 2002/0077550 | A1 | 6/2002 | Rabiner et al. |
| 2003/0129154 | A1 | 7/2003 | McDaniel |
| 2003/0157024 | A1 | 8/2003 | Tachibana et al. |
| 2004/0059265 | A1 | 3/2004 | Candy et al. |
| 2004/0162508 | A1 | 8/2004 | Uebelacker |
| 2004/0249271 | A1 * | 12/2004 | Besson .................. A61B 8/565 |
| | | | 600/427 |
| 2005/0010140 | A1 | 1/2005 | Forssmann |
| 2005/0038362 | A1 | 2/2005 | Schultheiss |
| 2005/0075587 | A1 | 4/2005 | Vago |
| 2005/0084519 | A1 | 4/2005 | Miyazaki |
| 2006/0051328 | A1 | 3/2006 | Johnson |
| 2006/0100550 | A1 | 5/2006 | Schultheiss et al. |
| 2006/0100552 | A1 * | 5/2006 | Schultheiss .......... A61H 23/008 |
| | | | 601/2 |
| 2006/0246044 | A1 | 11/2006 | Lutz |
| 2006/0293708 | A1 | 12/2006 | Moss |
| 2006/0293725 | A1 | 12/2006 | Rubinsky et al. |
| 2007/0142753 | A1 * | 6/2007 | Warlick .................. A61N 7/00 |
| | | | 601/2 |
| 2013/0197404 | A1 * | 8/2013 | Spector .............. A61B 17/2251 |
| | | | 601/15 |
| 2017/0128496 | A1 | 5/2017 | Williams et al. |
| 2017/0196766 | A1 * | 7/2017 | Spector .................. A61H 23/02 |
| 2017/0209708 | A1 | 7/2017 | Schwarz |

FOREIGN PATENT DOCUMENTS

| | | |
|---|---|---|
| WO | 2005018600 | 3/2005 |
| WO | 2005075020 | 8/2005 |
| WO | 2006023498 | 2/2006 |

OTHER PUBLICATIONS

Joelle Dupont, "Insulin signalling and lucose transport in the ovary and ovarian funciton during the ovarian cycle", 2016.*

Anna Weihs, "Shock Wave treatment enhances cell proliferation and improves wound healing by ATP release-coupled extracellular signal-regulated kinase (ERK) activation", 2014.*

Camilo Perez, Hong Chen, and Thomas J. Matula;Center for Industrial and Medical Ultrasound, Applied Physics Laboratory, University of Washington, 1013 NE 40th Street, Seattle, Washington 98105; Maria Karzova and Vera A. Khokhlovab; Department of Acoustics, Faculty of Physics, Moscow State University, Moscow 119991, Russia (Received Oct. 9, 2012; revised Apr. 16, 2013; accepted May 1, 2013) "Acoustic field characterization of the Duolith: Measurements and modeling of a clinical shock wave therapy device"; pp. 1663-1674.

Huemer, Georg M. et al.; "Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

R.Meirer, et al.; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier ltd.

T. Nishida, et al.; Extracorporeal Cardiac Shock Wave Therapy Markedly Ameliorates Ischemia-Induced Myocardial Dysfunction in Pigs in Vivo; Circulation; Nov. 9, 2004;Circulation. 2004; 110; pp. 3055-3061.

L.Gerdesmeyer, et al.; Antibacterial Effects of Extracorporeal Shock Waves;World Fed for Ultrasound in Medicine & Biology;printed USA;Elsevier, vol. 31,No. 1, pp. 115-119, 2005.

G.Haupt, et al.; Effect of Shock Waves on the Healing of Partial-Thickness Wounds in Piglets; Journal of Surgical Research, vol. 49, No. 1, pp. 45-48, Jul. 1990; Copyright 1990 by Academic Press, Inc.

Jagadeesh, G. et al.;"Novel applications of micro-shockwaves in biological sciences"; J. Indian Inst. Sci. 2002, 82, pp. 1-10.

Thiel, M. et al.; "The use of shock waves in medicine—a tool of the modem OR; an overview of basic physical principle?. history and research", Min Invas Ther & Allied Technol 2000; 9(3/4) 247-:253.

MERCK news release "FDA approves once-daily JANUVIA tm, the first and only DPP-4 inhibitor available in the United States for Type 2 Diabetes".

* cited by examiner

ACOUSTIC SHOCK WAVE THERAPEUTIC METHODS

TECHNICAL FIELD

The present invention relates to an improved method of utilizing acoustic shock waves for therapy of glands to modulate hormone production and release.

BACKGROUND OF THE INVENTION

In U.S. Pat. No. 7,470,240 B2, entitled "Pressure Pulse/Shock Wave Therapy Methods And An Apparatus For Conducting The Therapeutic Methods", is disclosed a novel use of unfocused shock waves to stimulate a cellular substance. From this patent a family of treatment patents evolved. The list includes U.S. Pat. Nos. 7,841,995; 7,883,482; 7,905,845 all divisional applications; and U.S. Pat. No. 7,507,213 entitled "Pressure Pulse/Shock Wave Therapy Methods For Organs"; U.S. Pat. No. 7,544,171 B2 entitled "Methods for Promoting Nerve Regeneration and Neuronal Growth and Elongation"; U.S. Pat. No. 7,988,648 B2 entitled "Pancreas Regeneration Treatment For Diabetics Using Extracorporeal Acoustic Shock Waves"; all teaching a new useful way to deliver acoustic shock waves to achieve a healing response. Each of these patents are incorporated herein by reference in their entirety. In addition, U.S. Pat. Nos. 8,257,282 and 8,535,249 for the device to perform these methods by delivering low energy unfocused acoustic shock waves to the cellular tissue being treated.

While this large volume of research has been rewarded by the granting of numerous patents, much new work has been evolving as the understanding of the technology is being applied. It is in this latest work that some, heretofore, unknown improvements and refinements have been discovered that were hidden from and unappreciated by scientists in this field. In particular, the use of acoustic shock waves to regulate and in some cases stimulate glandular hormonal secretions or modulate glandular hormonal secretions.

SUMMARY OF THE INVENTION

A method of modulating glandular secretions by administering acoustic shock waves to a gland, includes the steps of activating acoustic shock waves of an acoustic shock wave generator to emit acoustic shock waves and subjecting the gland to acoustic shock waves stimulating the gland to have a modulated response. The modulated response is one of an adjustment in hormonal release which increases low level output, decreases high level output or stabilizes erratic output. The emitted acoustic shock waves are focused or unfocused acoustic shock waves, or acoustic pressure waves, generated electrohydraulically, electromagnetically, radially, or via a piezo electric generating system. There may be other methods developed to generate a shockwave or acoustic wave. These methods should be covered as well as the patent is for the shock wave itself. The glands of the endocrine system lie within a patient's body and underlies the patient's skin. The shock wave generator is acoustically coupled to the patient's skin using a coupling gel or liquid, or an offset like a silicon device that can redirect or shape the acoustic shock wave. The gland is one of a testicle, ovary, pituitary gland, adrenal gland, thyroid gland, thymus, pineal gland, parathyroid, or hypothalamus. The method can be repeated one or more times. It is understood that the treatment may not be a permanent cure. The treatments must be performed regularly. As an example, the current standard of care for testosterone replacement therapy requires weekly injections to maintain increased testosterone levels. Our therapy is believed to offer longer periods of time between retreatments but may also require weekly treatments.

The stimulating of the gland causes a release of nitric oxide and growth factors including, but not limited to VGEF. The stimulating of the gland causes new blood vessels to be created increasing vascularization. It is also understood that acoustic shock waves cause a cells membrane to become permeable allowing for the exchange of certain proteins with surrounding cells. It is also known that shock waves cause exosomes to be released containing proteins and RNA. These releases stimulate a biologic cascade that includes the recruitment and activation of stem cells, including localized stem cells, and those recruited from a bodies own bone marrow and fat deposits, among other sites that store stem cells. It is known that shock waves stimulate, produce, or recruit stem cell attractants. These attractants call for other stem cells to migrate to the site treated with acoustic waves whereas the stem cell activate and differentiate. Additionally, shock waves modulate the inflammatory system via the toll like receptor 3 channels (TLR3). This inflammatory control is also critical to the shock wave's ability to modulate the glandular release of hormones. Glands that are over or under inflamed do not function optimally. The emitted acoustic shock waves are waves having an energy in the range of 0.01 $mJ/mm^2$ to 0.4 $mJ/mm^2$, preferably, the emitted acoustic shock waves are waves having an energy density in the range of 0.04 $mJ/mm^2$ to 0.3 $mJ/mm^2$ depending on the condition of the targeted gland and the depth of the gland from the skin's surface. The method has the gland receiving between 100 and 2000 acoustic shock waves during each treatment. The number of treatments during each therapy ranges from 1 to 12 sessions depending on the gland and the severity of the condition.

In one embodiment, the gland is a testicle. The modulated response is an increase in a hormonal release of testosterone wherein the patient was exhibiting low levels of testosterone. Symptoms of low levels of testosterone include lethargy, limited sex drive, and premature aging. A patient's sexual organ, including testicles may actually atrophy, or shrink. After therapy all or some of these symptoms would be reversed. The penis could lengthen as well as the size of the testicles.

In another embodiment, the gland is an adrenal gland. The modulated response is a decrease in a hormonal release of adrenaline wherein the patient was exhibiting excessive levels of adrenaline. Symptoms of too much adrenaline release is high anxiety or panic attacks, including the fight or flight symptoms (partial list of symptoms). After therapy, these symptoms should be modulated.

Based on the depth of the glands within a patient's body and the potential range of shock wave emitting devices, focused, unfocused, planar, etc.; the successful targeting of the gland may require the addition of x ray or ultrasound. A preferred embodiment of this invention includes the incorporation of a 3-Dimensional ultrasound system that allows the practitioner to see the targeted gland in cross hairs on the practitioner's 3D ultrasound system. The inventor's proprietary software system integrates the shock wave probe (fixed or hand held) with the ultrasound system such that wherever the probe is targeted the practitioner will see the targeted area on their ultrasound screen.

Definitions

"Adrenal Gland": The adrenal glands (also known as suprarenal glands) are endocrine glands that produce a variety of hormones including adrenaline and the steroids aldosterone and cortisol. They are found above the kidneys. Each gland has an outer cortex which produces steroid hormones and an inner medulla.

"Adrenaline": Adrenaline, also known as adrenalin or epinephrine, is a hormone, neurotransmitter, and medication. Epinephrine is normally produced by both the adrenal glands and certain neurons. It plays an important role in the fight-or-flight response by increasing blood flow to muscles, output of the heart, pupil dilation, and blood sugar.

"Aldosterone": Aldosterone, the main mineralocorticoid hormone, is a steroid hormone produced by the zona glomerulosa of the adrenal cortex in the adrenal gland. It is essential for sodium conservation in the kidney, salivary glands, sweat glands and colon. It plays a central role in the homeostatic regulation of blood pressure, plasma sodium (Na+), and potassium (K+) levels. It does so mainly by acting on the mineralocorticoid receptors in the distal tubules and collecting ducts of the nephron. It influences the reabsorption of sodium and excretion of potassium (from and into the tubular fluids, respectively) of the kidney, thereby indirectly influencing water retention or loss, blood pressure and blood volume. When dysregulated, aldosterone is pathogenic and contributes to the development and progression of cardiovascular and renal disease.

"Cortisol": Cortisol is a steroid hormone, in the glucocorticoid class of hormones. When used as a medication, it is known as hydrocortisone. It is produced in humans by the zona fasciculata of the adrenal cortex within the adrenal gland. It is released in response to stress and low blood-glucose concentration. It functions to increase blood sugar through gluconeogenesis, to suppress the immune system, and to aid in the metabolism of fat, protein, and carbohydrates. It also decreases bone formation.

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"Estrogen": A female steroid hormone that is produced by the ovaries and, in lesser amounts, by the adrenal cortex, placenta, and male testes. Estrogen helps control and guide sexual development, including the physical changes associated with puberty. It also influences the course of ovulation in the monthly menstrual cycle, lactation after pregnancy, aspects of mood, and the aging process. Production of estrogen changes naturally over the female lifespan, reaching adult levels with the onset of puberty (menarche) and decreasing in middle age until the onset of menopause. Estrogen deficiency can lead to lack of menstruation (amenorrhea), persistent difficulties associated with menopause (such as mood swings and vaginal dryness), and osteoporosis in older age. In cases of estrogen deficiency, natural and synthetic estrogen preparations may be prescribed. Estrogen is also a component of many oral contraceptives. An overabundance of estrogen in men causes development of female secondary sexual characteristics (feminization), such as enlargement of breast tissue.

"extracorporeal" occurring or based outside the living body.

A "generalized paraboloid" according to the present invention is also a three-dimensional bowl. In two dimensions (in Cartesian coordinates, x and y) the formula $yn=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of $(p(-z,+z))$, with z being a measure for the burn down of an electrode, and n, so that phenomena including, but not limited to, burn down of the tip of an electrode $(-z,+z)$ and/or disturbances caused by diffraction at the aperture of the paraboloid are compensated for.

"Hormone": A hormone is any member of a class of signaling molecules produced by glands in multicellular organisms that are transported by the circulatory system to target distant organs to regulate physiology and behaviour. Hormones have diverse chemical structures, mainly of 3 classes: eicosanoids, steroids, and amino acid/protein derivatives (amines, peptides, and proteins). The glands that secrete hormones comprise the endocrine signaling system. The term hormone is sometimes extended to include chemicals produced by cells that affect the same cell (autocrine or intracrine signalling) or nearby cells (paracrine signalling). Hormones are used to communicate between organs and tissues for physiological regulation and behavioral activities, such as digestion, metabolism, respiration, tissue function, sensory perception, sleep, excretion, lactation, stress, growth and development, movement, reproduction, and mood. Hormones affect distant cells by binding to specific receptor proteins in the target cell resulting in a change in cell function. When a hormone binds to the receptor, it results in the activation of a signal transduction pathway that typically activates gene transcription resulting in increased expression of target proteins; non-genomic effects are more rapid, and can be synergistic with genomic effects. Amino acid-based hormones (amines and peptide or protein hormones) are water-soluble and act on the surface of target cells via second messengers; steroid hormones, being lipid-soluble, move through the plasma membranes of target cells (both cytoplasmic and nuclear) to act within their nuclei. Hormone secretion may occur in many tissues. Endocrine glands are the cardinal example, but specialized cells in various other organs also secrete hormones. Hormone secretion occurs in response to specific biochemical signals from a wide range of regulatory systems. For instance, serum calcium concentration affects parathyroid hormone synthesis; blood sugar (serum glucose concentration) affects insulin synthesis; and because the outputs of the stomach and exocrine pancreas (the amounts of gastric juice and pancreatic juice) become the input of the small intestine, the small intestine secretes hormones to stimulate or inhibit the stomach and pancreas based on how busy it is. Regulation of hormone synthesis of gonadal hormones, adrenocortical hormones, and thyroid hormones is often dependent on complex sets of direct influence and feedback interactions involving the hypothalamic-pituitary-adrenal (HPA), -gonadal (HPG), and -thyroid (HPT) axes. Upon secretion, certain hormones, including protein hormones and catecholamines, are water-soluble and are thus readily transported through the circulatory system. Other hormones, including steroid and thyroid hormones, are lipid-soluble; to allow for their widespread distribution, these hormones must bond to carrier plasma glycoproteins (e.g., thyroxine-binding globulin (TBG)) to form ligand-protein complexes. Some hormones are completely active when released into the bloodstream (as is the case for insulin and growth hormones), while others are prohormones that must be activated in specific cells through a series of activation steps that are commonly highly regulated. The endocrine system secretes hormones directly into the bloodstream typically into fenestrated capillaries, whereas the exocrine system secretes its hormones indirectly using ducts. Hormones with paracrine function diffuse through the interstitial spaces to nearby target tissue.

"Hypothalamus": The hypothalamus is a portion of the brain that contains a number of small nuclei with a variety of functions. One of the most important functions of the hypothalamus is to link the nervous system to the endocrine system via the pituitary gland (hypophysis). The hypothalamus is located below the thalamus and is part of the limbic system.

"Melatonin": Melatonin, also known as N-acetyl-5-methoxy tryptamine, is a hormone that is produced by the pineal gland in animals and regulates sleep and wakefulness. In animals, melatonin is involved in the entrainment (synchronization) of the circadian rhythms including sleep-wake timing, blood pressure regulation, seasonal reproduction, and many others. Many of its biological effects in animals are produced through activation of melatonin receptors, while others are due to its role as an antioxidant, with a particular role in the protection of nuclear and mitochondrial DNA.

A "paraboloid" according to the present invention is a three-dimensional reflecting bowl. In two dimensions (in Cartesian coordinates, x and y) the formula $y2=2px$, wherein $p/2$ is the distance of the focal point of the paraboloid from its apex, defines the paraboloid. Rotation of the two-dimensional figure defined by this formula around its longitudinal axis generates a de facto paraboloid.

"Parathyroid": Parathyroid glands are small endocrine glands in the neck of humans and other tetrapods that produce parathyroid hormone. Humans usually have four parathyroid glands, variably located on the back of the thyroid gland. Parathyroid hormone and calcitonin (one of the hormones made by the thyroid gland) have key roles in regulating the amount of calcium in the blood and within the bones.

"Parathyroid Hormone": Parathyroid hormone (PTH), also called parathormone or parathyrin, is a hormone secreted by the parathyroid glands that is important in bone remodeling, which is an ongoing process in which bone tissue is alternately resorbed and rebuilt over time. PTH is secreted in response to low blood serum calcium (Ca2+) levels. PTH indirectly stimulates osteoclast activity within bone marrow, in an effort to release more ionic calcium (Ca2+) into the blood to elevate serum calcium (Ca2+) levels. The bones act as a (metaphorical) "bank of calcium" from which the body can make "withdrawals" as needed to keep the amount of calcium in the blood at appropriate levels despite the ever-present challenges of metabolism, stress, and nutritional variations. PTH is "a key that unlocks the bank vault" to remove the calcium. In consequence, PTH is vital to health, and health problems that yield too little or too much PTH (such as hypoparathyroidism, hyperparathyroidism, or paraneoplastic syndromes) can wreak havoc in the form of bone disease, hypocalcaemia, and hypercalcaemia.

"Pineal body": Pineal gland, also called conarium, epiphysis cerebri, pineal organ, or pineal body, endocrine gland. The pineal gland is a small endocrine gland in the vertebrate brain. The pineal gland produces melatonin, a serotonin-derived hormone which modulates sleep patterns in both circadian and seasonal cycles. The shape of the gland resembles a pine cone, hence its name. The pineal gland is located in the epithalamus, near the center of the brain, between the two hemispheres, tucked in a groove where the two halves of the thalamus join.

"Pituitary gland": In vertebrate anatomy, the pituitary gland, or hypophysis, is an endocrine gland about the size of a pea and weighing 0.5 grams (0.018 oz) in humans. It is a protrusion off the bottom of the hypothalamus at the base of the brain. The hypophysis rests upon the hypophysial fossa of the sphenoid bone in the center of the middle cranial fossa and is surrounded by a small bony cavity (sella turcica) covered by a dural fold (diaphragma sellae). The anterior pituitary (or adenohypophysis) is a lobe of the gland that regulates several physiological processes (including stress, growth, reproduction, and lactation). The intermediate lobe synthesizes and secretes melanocyte-stimulating hormone. The posterior pituitary (or neurohypophysis) is a lobe of the gland that is functionally connected to the hypothalamus by the median eminence via a small tube called the pituitary stalk (also called the infundibular stalk or the infundibulum). Hormones secreted from the pituitary gland help control: growth, blood pressure, management of energy, all functions of the sex organs, thyroid glands and metabolism as well as some aspects of pregnancy, childbirth, nursing, water/salt concentration at the kidneys, temperature regulation and pain relief.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (µs) for the positive part of a cycle and typically above some micro-seconds for the negative part of a cycle.

"Reproductive glands" include ovaries and testes: A woman's 2 ovaries are located on each side of the uterus, just below the opening of the fallopian tubes (tubes that extend from the uterus to near the ovaries). The ovaries contain the egg cells needed for reproduction. They also make estrogen and progesterone. These affect many of the female characteristics and reproductive functions. Estrogens also play an important role in bone health and strength. The levels of estrogen and progesterone are controlled by certain hormones made by the pituitary gland. The testes are oval-shaped organs that hang suspended in a pouch of skin (scrotum) outside the male body. The testes are the site of sperm production. They also make testosterone and other hormones. These affect many of the male characteristics and support sperm production. Testosterone also plays an important role in bone health and strength.

"Shock Wave": As used herein is defined by Camilo Perez, Hong Chen, and Thomas J. Matula; Center for Industrial and Medical Ultrasound, Applied Physics Laboratory, University of Washington, 1013 NE 40th Street, Seattle, Wash. 98105; Maria Karzova and Vera A. Khokhlovab; Department of Acoustics, Faculty of Physics, Moscow State University, Moscow 119991, Russia; (Received 9 Oct. 2012; revised 16 Apr. 2013; accepted 1 May 2013) in their publication, "Acoustic field characterization of the Duolith: Measurements and modeling of a clinical shock wave therapy device"; incorporated by reference herein in its entirety.

"Testosterone": Testosterone is the primary male sex hormone and an anabolic steroid. In male humans, testosterone plays a key role in the development of male reproductive tissues such as testes and prostate, as well as promoting secondary sexual characteristics such as increased muscle and bone mass, and the growth of body hair. In addition, testosterone is involved in health and well-being, and the prevention of osteoporosis. Insufficient levels of testosterone in men may lead to abnormalities including frailty and bone loss. Testosterone is a steroid from the androstane class containing a keto and hydroxyl groups at the three and seventeen positions respectively. It is biosynthesized in several steps from cholesterol and is converted in the liver to inactive metabolites. It exerts its action through binding to and activation of the androgen receptor. In humans and most other vertebrates, testosterone is secreted primarily by the testicles of males and, to a lesser extent, the ovaries of females. On average, in adult males, levels of testosterone are about 7 to 8 times as great as in adult females. As the metabolism of testosterone in males is greater, the daily production is about 20 times greater in men. Females are also more sensitive to the hormone.

"Thymus": The thymus is a specialized primary lymphoid organ of the immune system. Within the thymus, T cells mature. T cells are critical to the adaptive immune system, where the body adapts specifically to foreign invaders. The thymus is composed of two identical lobes and is located anatomically in the anterior superior mediastinum, in front of the heart and behind the sternum. Histologically, each lobe of the thymus can be divided into a central medulla and a peripheral cortex which is surrounded by an outer capsule. The cortex and medulla play different roles in the development of T cells. Cells in the thymus can be divided into thymic stromal cells and cells of hematopoietic origin (derived from bone marrow resident hematopoietic stem cells). Developing T cells are referred to as thymocytes and are of hematopoietic origin. Stromal cells include epithelial cells of the thymic cortex and medulla, and dendritic cells. The thymus provides an inductive environment for development of T cells from hematopoietic progenitor cells. In addition, thymic stromal cells allow for the selection of a functional and self-tolerant T cell repertoire. Therefore, one of the most important roles of the thymus is the induction of central tolerance. The thymus is largest and most active during the neonatal and pre-adolescent periods. By the early teens, the thymus begins to atrophy and thymic stroma is mostly replaced by adipose (fat) tissue. Nevertheless, residual T lymphopoiesis continues throughout adult life.

"Thyroid": The thyroid gland, or simply the thyroid, is an endocrine gland in the neck, consisting of two lobes connected by an isthmus. It is found at the front of the neck, below the Adam's apple. The thyroid gland secretes thyroid hormones, which primarily influence the metabolic rate and protein synthesis. The hormones also have many other effects including those on development. The thyroid hormones triiodothyronine (T3) and thyroxine (T4) are created from iodine and tyrosine. The thyroid also produces the hormone calcitonin, which plays a role in calcium homeostasis. Hormonal output from the thyroid is regulated by thyroid-stimulating hormone (TSH) secreted from the anterior pituitary gland, which itself is regulated by thyrotropin-releasing hormone (TRH) produced by the hypothalamus. The thyroid may be affected by several diseases. Hyperthyroidism occurs when the gland produces excessive amounts of thyroid hormones, the most common cause being Graves' disease, an autoimmune disorder. In contrast, hypothyroidism is a state of insufficient thyroid hormone production. Worldwide, the most common cause is iodine deficiency. Thyroid hormones are important for development, and hypothyroidism secondary to iodine deficiency remains the leading cause of preventable intellectual disability. In iodine-sufficient regions, the most common cause of hypothyroidism is Hashimoto's thyroiditis, also an autoimmune disorder. In addition, the thyroid gland may also develop several types of nodules and cancer.

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1A:
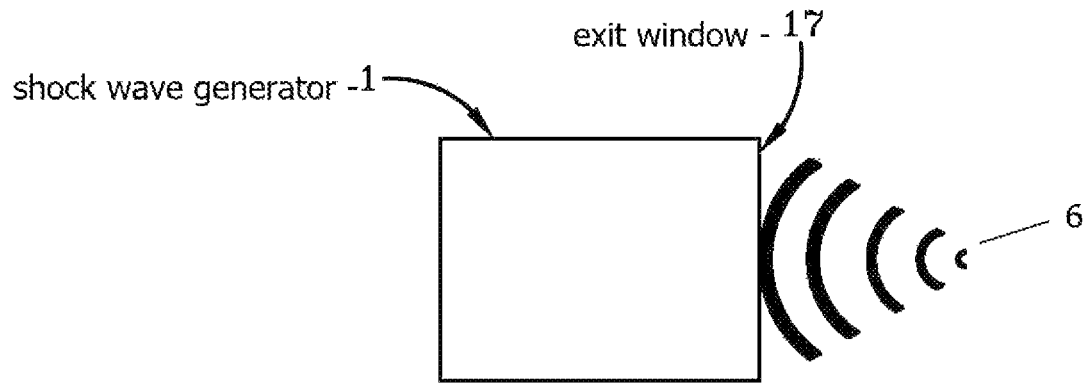
FIG. 1a is a simplified depiction of a pressure pulse/shock wave (PP/SW) generator with focusing wave characteristics.

The present methodology uses an acoustic shock wave form directed to specific glands to stimulate a modulated response.

In the Extracorporeal Shock wave method of treating a patient at a target site on the anatomy. In this invention, the term target site refers to a location of a specific gland and the tissue in the path of the gland and the shock wave applicator. the patient is placed in a convenient orientation to permit the source of the emitted waves to most directly send the waves to the target site to initiate shock wave stimulation of the target area. Assuming the target area is within a projected area of the wave transmission, a single transmission dosage of wave energy may be used. The transmission dosage can be from a few seconds to 20 minutes or more dependent on the condition. Preferably the waves are generated from an unfocused or focused source. The unfocused waves can be divergent or near planar and having a low-pressure amplitude and density in the range of 0.00001 $mJ/mm^2$ to 1.0 $mJ/mm^2$ or less, most typically below 0.2 $mJ/mm^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and in some cases, such as unfocused low energy, and even low energy focused emissions can be accomplished without creating the cavitation bubbles in the tissue of the target site. This effectively insures the patient does not have to experience the sensation of pain so common in the higher energy focused wave forms having a focal point at or within the targeted treatment site.

Accordingly, unless for other reasons such as a trauma or immediate post-operative shock wave therapy no localized or general anesthesia is required.

If the target site is within the body it may be such that the patient or the generating source must be reoriented relative to the site and a second, third or more treatment dosage can be administered. The fact that the dosage is at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments. Alternatively, the wave source generators may be deployed in an array wherein the subject patient is effectively enveloped or surrounded by a plurality of low energy wave source generators which can be simultaneously bombarding the target site from multiple directions.

The goal in such treatments is to provide 2000 to 6000 acoustic shock waves at a voltage of 14 kV to 28 kV across a spark gap generator in a single treatment preferably or one or more adjuvant treatments by targeting the site impinging the emitted waves on the target.

The present method, in many cases, does not rely on precise site location per se. The physician's general understanding of the anatomy of the patient should be sufficient to locate the target site to be treated. The treated area can withstand a far greater number of shock waves based on the selected energy level being emitted. For example, at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating cellular release or activation of VEGF and other growth factors and most importantly to modulate and regulate hormonal secretions from a specific targeted gland. In other cases where the precise location must be known, the use of an applicator acoustic wave emission is directed by an ultrasound image, preferably the applicator has a software program coupled to the imaging device to allow the doctor to visualize the area being treated. The applicator can be hand held or manipulated in a fixture, if so desired, in either way the doctor can see the gland being treated and the image reflects the path of the wave transmission.

A key advantage of the present inventive methodology is that it is complimentary to conventional medical procedures. In the case of any post-operative surgical procedure the surgical area of the patient can be post operatively bombarded with these low energy waves to stimulate cellular release of healing agents and growth factors. Most preferably such patients may be provided more than one such ESWT treatment with an intervening dwell time for cellular relaxation prior to secondary and tertiary treatments.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly, not only can the energy intensity be reduced but also the number of applied shock wave impulses can be lowered from several thousand to as few as one or more pulses and still yield a beneficial stimulating response. This allows acoustic wave therapies to be directed to a specific endocrine gland being treated with confidence the signal will be fed back to the entire system via the pituitary gland (hypophysis). This use of acoustic wave stimulation allows a therapy to be given to modulate and adjust glandular secretions of hormones to be regulated and adjusted to achieve a desired adjustment, for example if too low to increase specific secretions, if too high to lessen these secretions.

The biological model motivated the design of sources with low pressure amplitudes and energy densities. First: spherical waves generated between two tips of an electrode; and second: nearly even waves generated by generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern or a nearly planar wave pattern and can be used in isolation or in combination with focused wave patterns yielding to an improved therapeutic treatment capability that is non-invasive with few if any disadvantageous contraindications. Alternatively, a focused wave emitting treatment may be used wherein the focal point extends to the gland or target site, preferably beyond the target treatment site or gland, potentially external to the patient. In any event, the beam of acoustic waves transmitted needs to project in a large enough area to be effective to the gland. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factor thereby inducing or accelerating healing to achieve a proper regulated glandular response.

The unfocused shock waves can be of a divergent wave pattern or near planar pattern preferably of a low peak pressure amplitude and density. Typically, the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the human or animal torso and the treatment site can be defined by a much larger treatment area than the 0.10-3.0 $cm^2$ commonly produced by focused waves. The above methodology is particularly well suited for surface as well as sub-surface soft tissue treatments.

The above methodology is valuable in generation of tissue, vascularization and may be used in combination with stem cell therapies as well as regeneration of tissue and vascularization.

The following invention description first provides a detailed explanation of acoustic shock waves, as illustrated in FIGS. 1a-12. As used herein an acoustic shock wave is an asymmetric wave with an exceptionally rapid peak rise time and slower return time from the peak amplitude. Historically, these acoustic shock waves were first used medically to destroy kidney stones. The wave patterns were directed to a focal point with ah a relatively high energy to blast the concrements into small urinary tract passable fragments.

A whole class of acoustic shock waves for medical treatments were later discovered that employed low energy acoustic shock waves. These low energy acoustic shock waves maintained the asymmetric wave profile, but at much lower energies as described in US2006/0100550 which is incorporated herein in its entirety.

These low energy acoustic shock waves advantageously could stimulate a substance without requiring a focused beam. The advantage of such an unfocused beam was the acoustic wave could be directed to pass through tissue without causing any cell rupturing which would be evidenced by a lack of a hematoma or bruising. This use of unfocused, low energy acoustic shock waves provided an ability to treat a large volume of tissue virtually painlessly.

The use of low energy acoustic shock waves that employ a focused beam has been spurred on as a viable alternative to the unfocused low energy shock waves because the focal point being of a small point of energy has little or a small region of cell damage as the remaining portions of the wave pattern can provide a stimulating effect similar to the unfocused shock waves. Basically, the effect is the same with the users of focused waves achieving the benefits of the unfocused waves, but with a focal point of peak energy in a tiny localised region. So, for purposes of the present invention, the use of "soft waves" those defined by low energy beams will be applicable to both focused and unfocused beams o acoustic shock waves for the present invention.

One last and significant point that the reader must appreciate is that an "acoustic shock wave" is not an "ultrasound wave". Sonic or ultrasound waves are generated with a uniform and symmetrical wave pattern similar to a sinusoidal wave. This type of sonic wave causes a sheer action on tissue as evidenced by a generation of heat within the tissue, for this reason, the use of sonic waves of the ultrasonic type are not considered as efficient in cell survivability rates.

The present preferred invention avoids the use of such cell damaging sonic waves, most particularly in treating glands.

With reference to FIGS. 1a-12, a variety of schematic views of acoustic shock waves are described. The following description of the proper amplitude and pressure pulse intensities of the shock waves 200 are provided below along with a description of how the shock waves actually function and have been taken from the co-pending application of the present inventors and replicated herein as described below. For the purpose of describing the shock waves 200 were used as exemplary and are intended to include all of the wave patterns discussed in the figures as possible treatment patterns.

FIG. 1a is a simplified depiction of a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

Figure 1B:
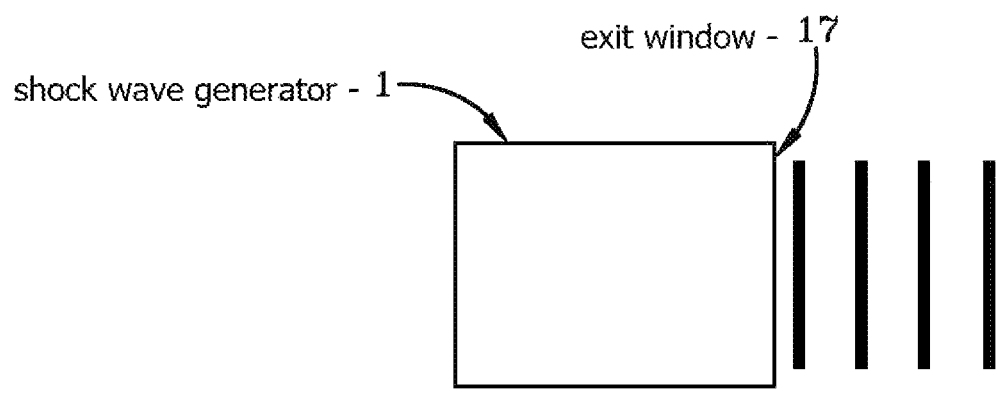
FIG. 1b is a simplified depiction of a pressure pulse/shock wave generator with plane wave characteristics.

FIG. 1b is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
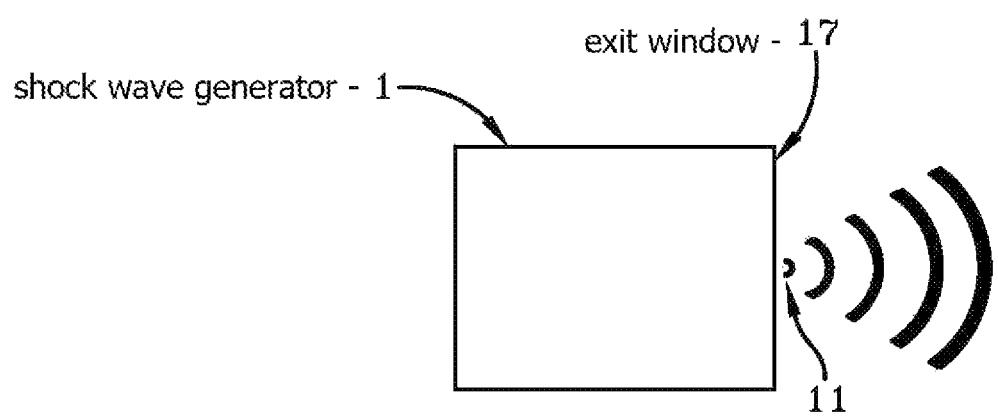
FIG. 1c is a simplified depiction of a pressure pulse/shock wave generator with divergent wave characteristics.

FIG. 1c is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1c the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2b.

Figure 2A:
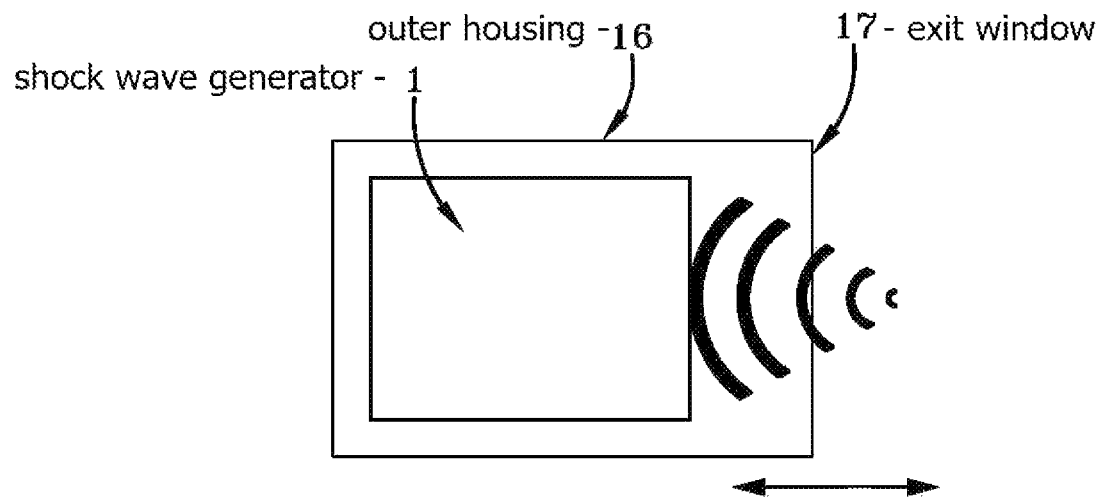
FIG. 2a is a simplified depiction of a pressure pulse/shock wave generator having an adjustable exit window along the pressure wave path. The exit window is shown in a focusing position.

FIG. 2a is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2a is similar to FIG. 1a but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2a shows the situation in which the arrangement transmits focused pressure pulses.

Figure 2B:
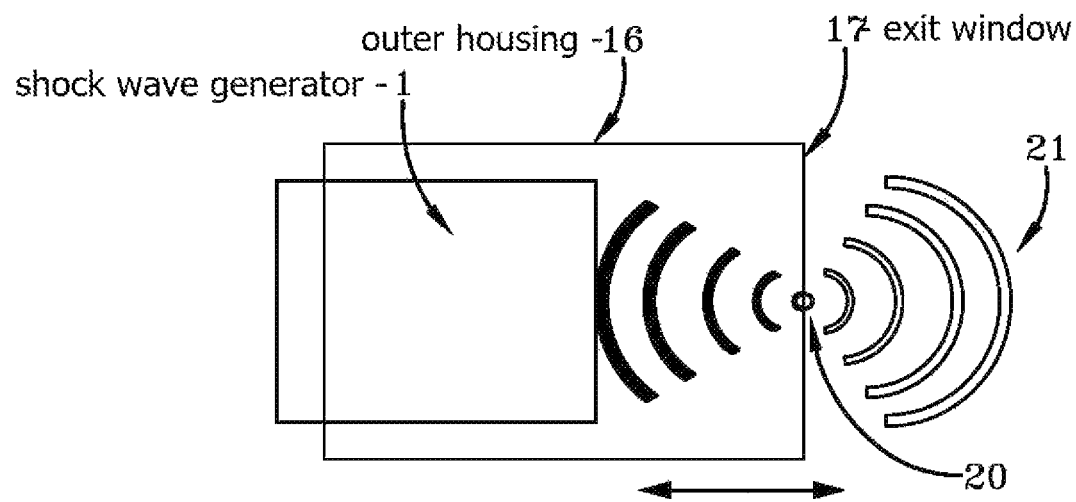
FIG. 2b is a simplified depiction of a pressure pulse/shock wave generator having an exit window along the pressure wave path. The exit window as shown is positioned at the highest energy divergent position.

FIG. 2b is a simplified depiction of the pressure pulse/shock wave generator (shock wave head) having an adjustable or exchangeable housing around the pressure wave path with the exit window 17 being in the highest energy divergent position. The configuration shown in FIG. 2b can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
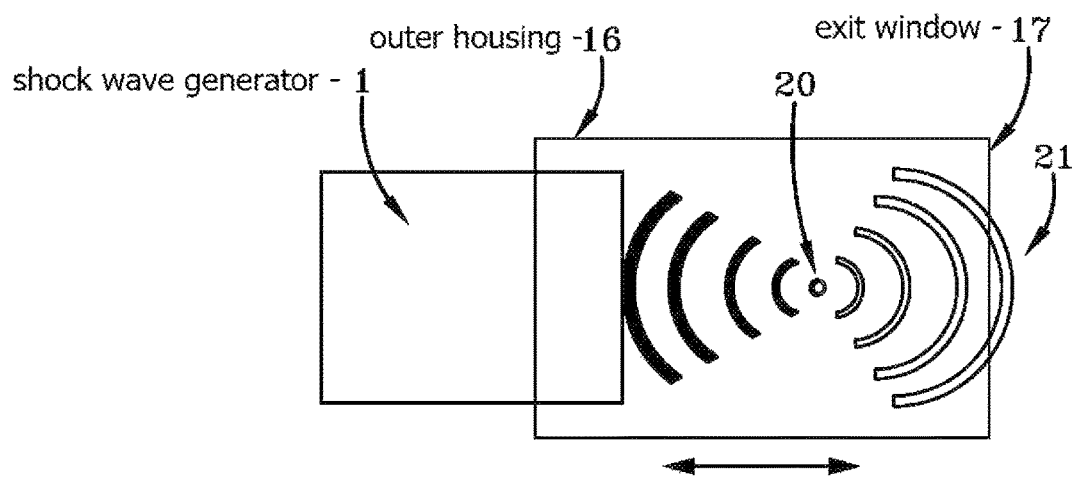
FIG. 2c is a simplified depiction of a pressure pulse/shock wave generator having an exit window along the pressure wave path. The exit window is shown at a low energy divergent position.

FIG. 2c is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, planar, nearly plane, convergent or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the various types of acoustic shock waves and types of shock wave generating heads provides versatility, the person skilled in the art will appreciate that apparatuses that produce low energy or soft acoustic shock waves having, for one example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
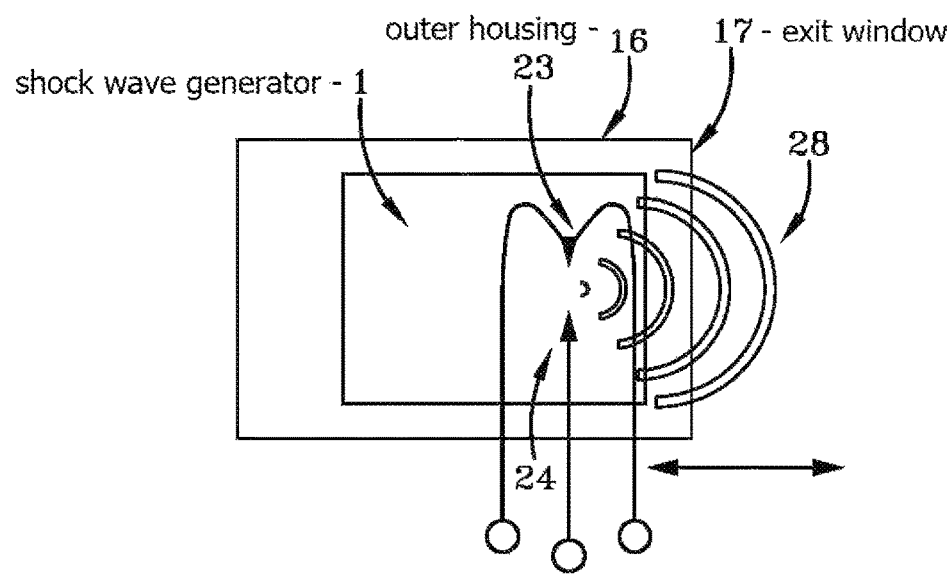
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
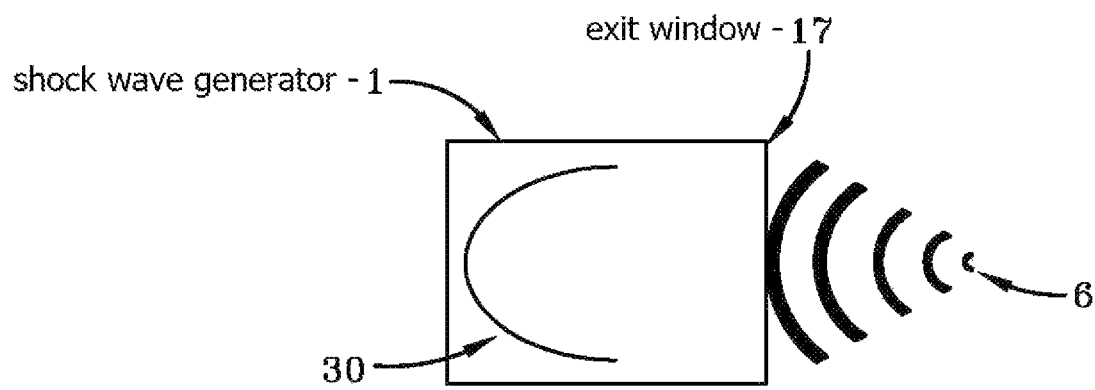
FIG. 4a is a simplified depiction of a pressure pulse/shock wave generator having a focusing element in the form of an ellipsoid. The waves generated are focused.

FIG. 4a is a simplified depiction of the pressure pulse/shock wave generator (shock wave head) having as focusing element an ellipsoid (30). Thus, the generated waves are focused at (6).

Figure 4B:
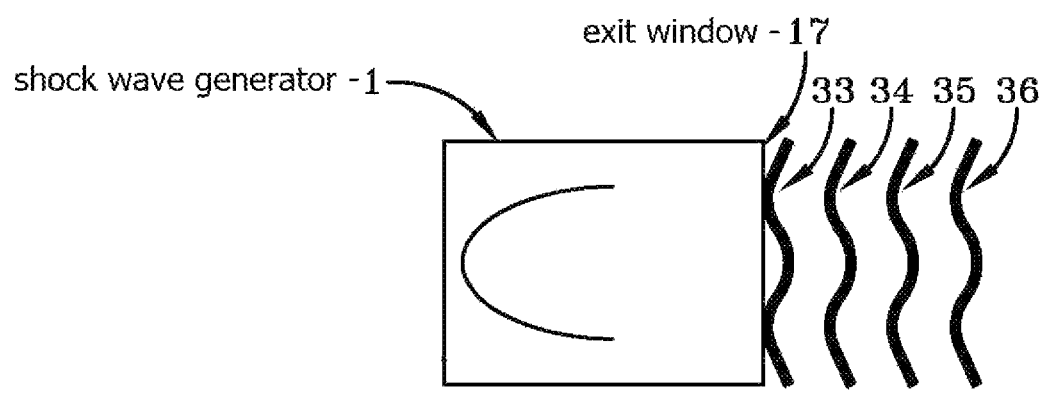
FIG. 4b is a simplified depiction of a pressure pulse/shock wave generator having a parabolic reflector element and generating waves that are disturbed plane.

FIG. 4b is a simplified depiction of the pressure pulse/shock wave generator (shock wave head) having as a focusing element an paraboloid (y2=2px). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
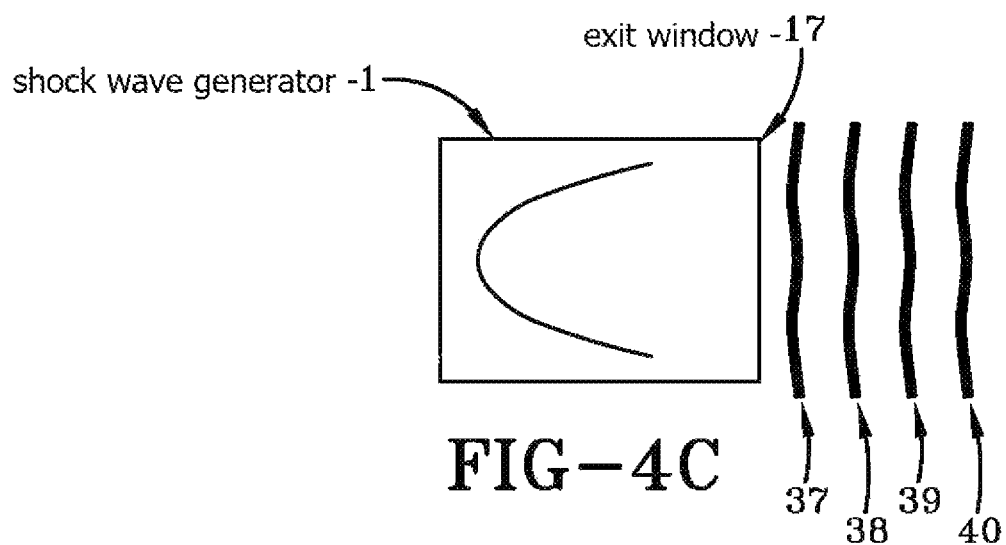
FIG. 4c is a simplified depiction of a pressure pulse/shock wave generator having a quasi parabolic reflector element (generalized paraboloid) and generating waves that are nearly plane/have nearly plane characteristics.

FIG. 4c is a simplified depiction of the pressure pulse/shock wave generator (shock wave head) having as a focusing element a generalized paraboloid (yn=2px, with 1.2<n<2.8 and n≠2). Thus, the characteristics of the wave fronts generated behind the exit window (37, 38, 39, and 40) are, compared to the wave fronts generated by a paraboloid (y2=2px), less disturbed, that is, nearly plane (or nearly parallel or nearly even (37, 38, 39, 40)). Thus, conformational adjustments of a regular paraboloid (y2=2px) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid (y2=2px) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

Figure 4D:
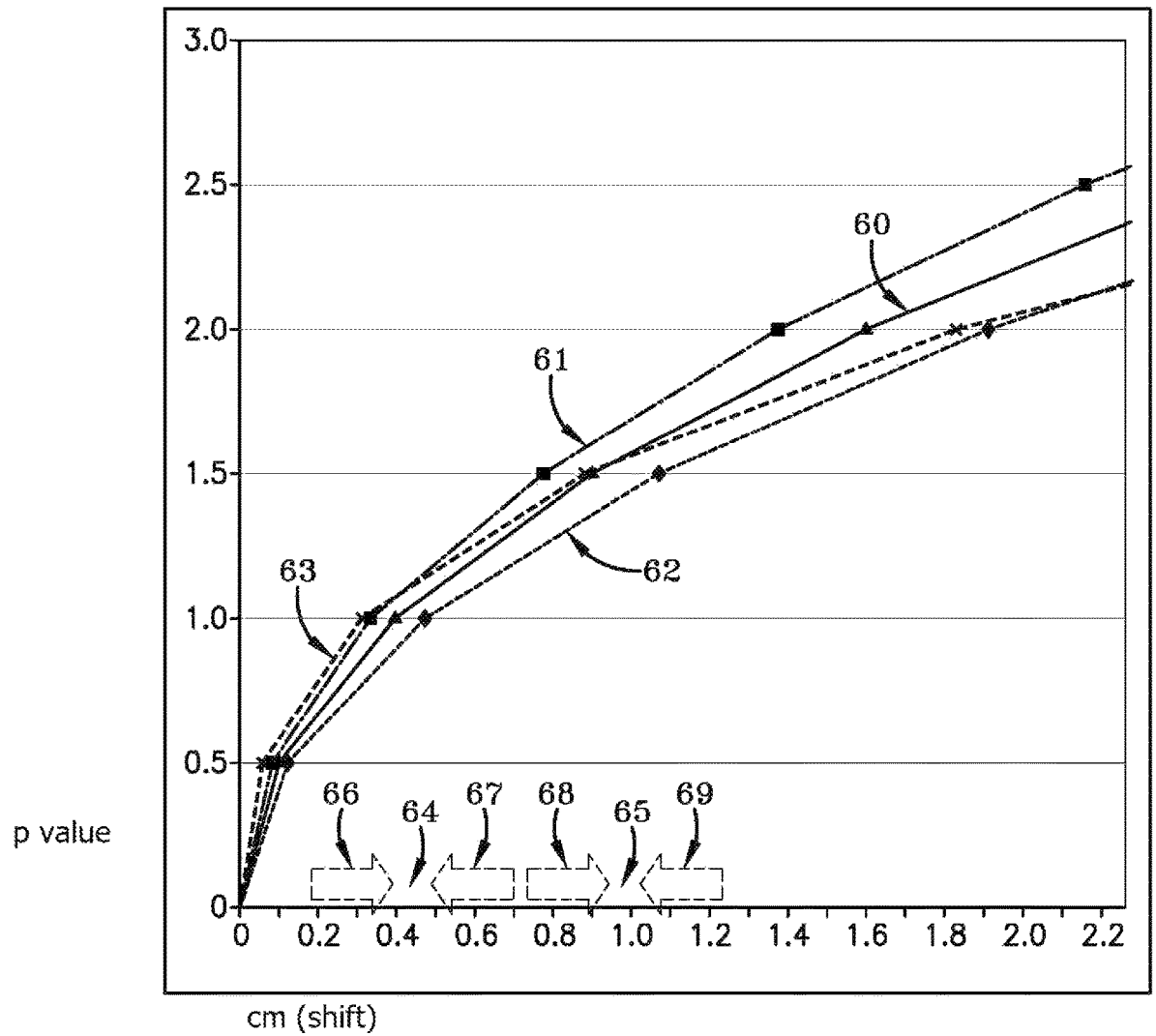
FIG. 4d is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4d shows sectional views of a number of paraboloids. Numeral 62 indicates a paraboloid of the shape y2=2px with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62. This particular generalized paraboloid was generated by choosing a value of n≠2 and a p value of about 1.55 cm. The generalized paraboloid compensates for different p values that result from the electrode burn down and/or adjustment of the electrode tips.

Figure 5:
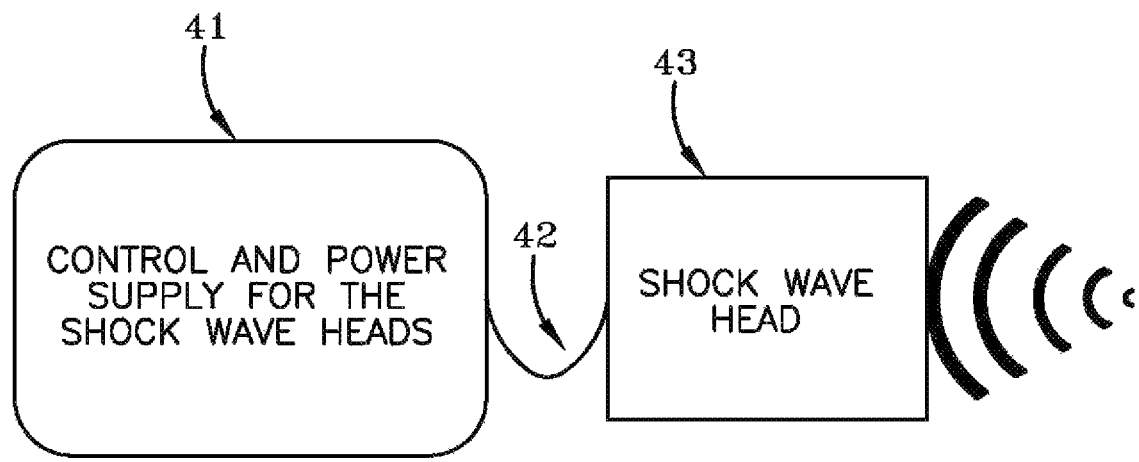
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
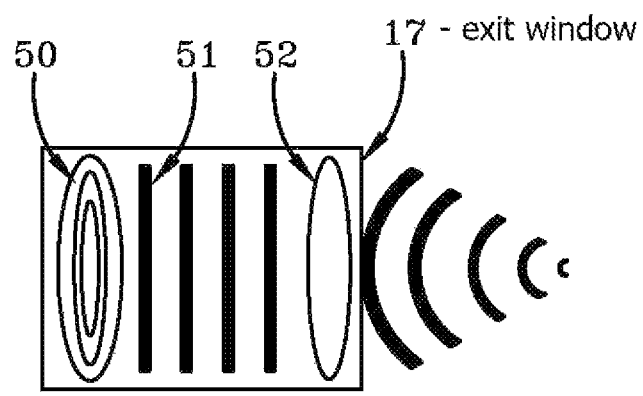
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
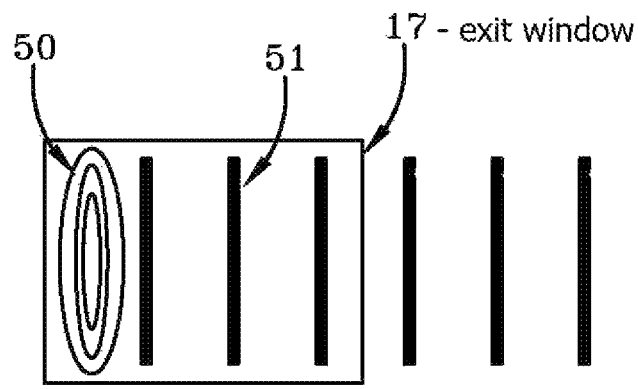
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
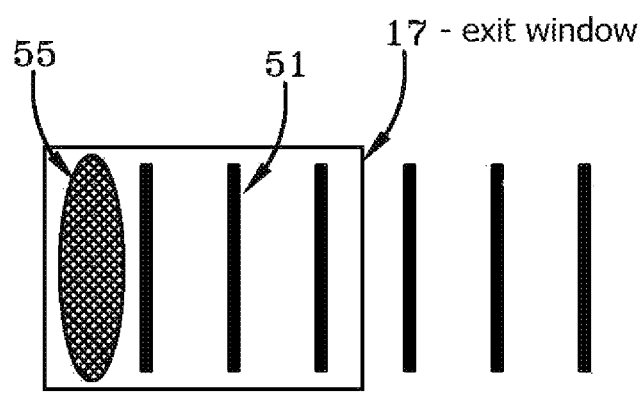
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. 4a to 4c as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
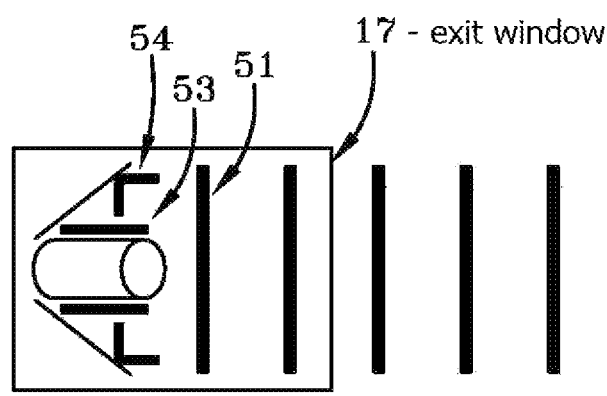
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
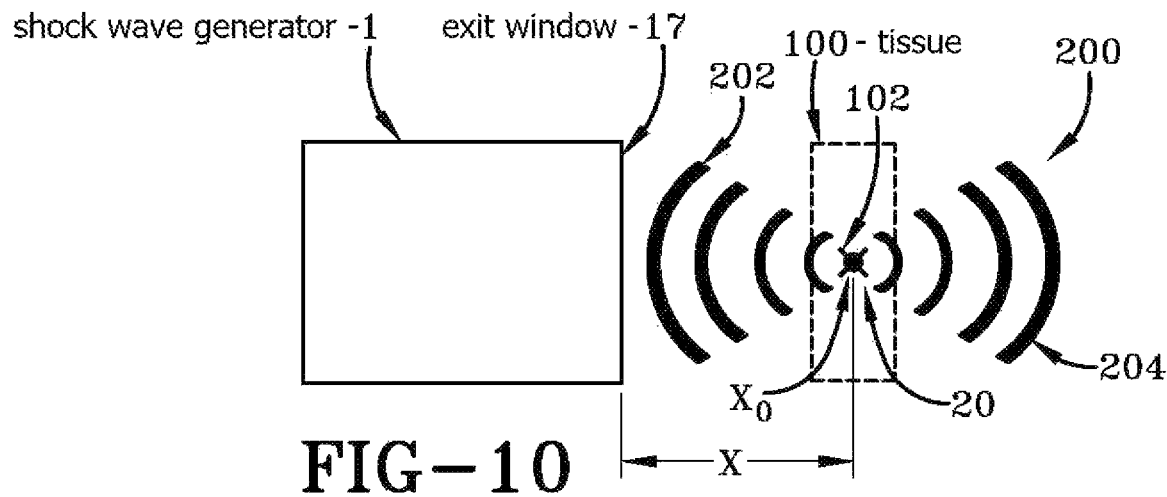
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
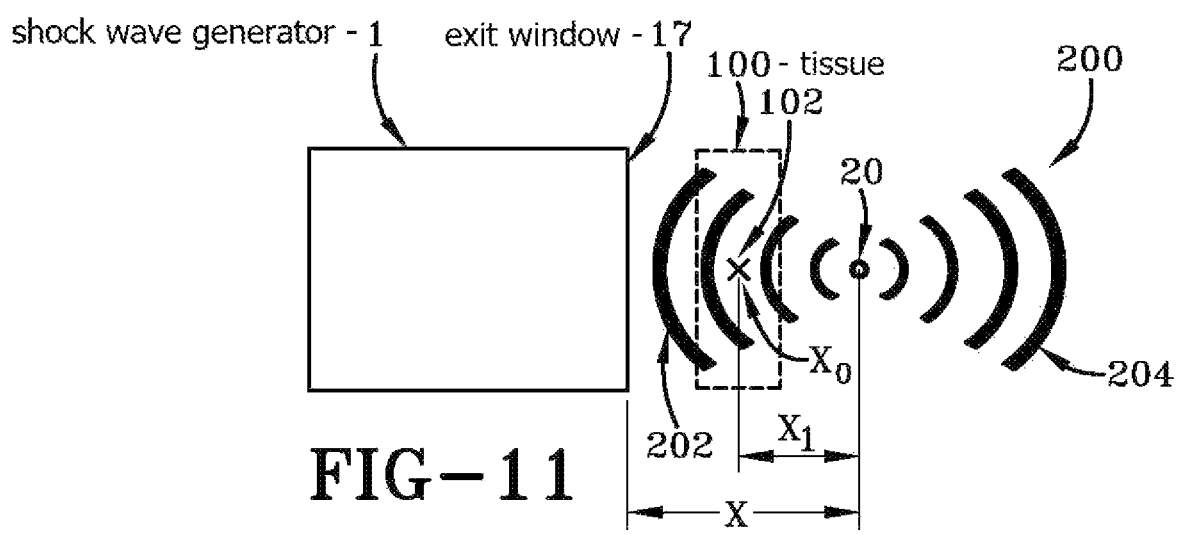
FIG. 11 is a simplified depiction of a pressure pulse/shock wave (PP/SW) generator with the focusing wave characteristics shown wherein the focus is located a distance X, from the location $X_0$ of an organ wherein the converging waves impinge the organ.
Figure 12:
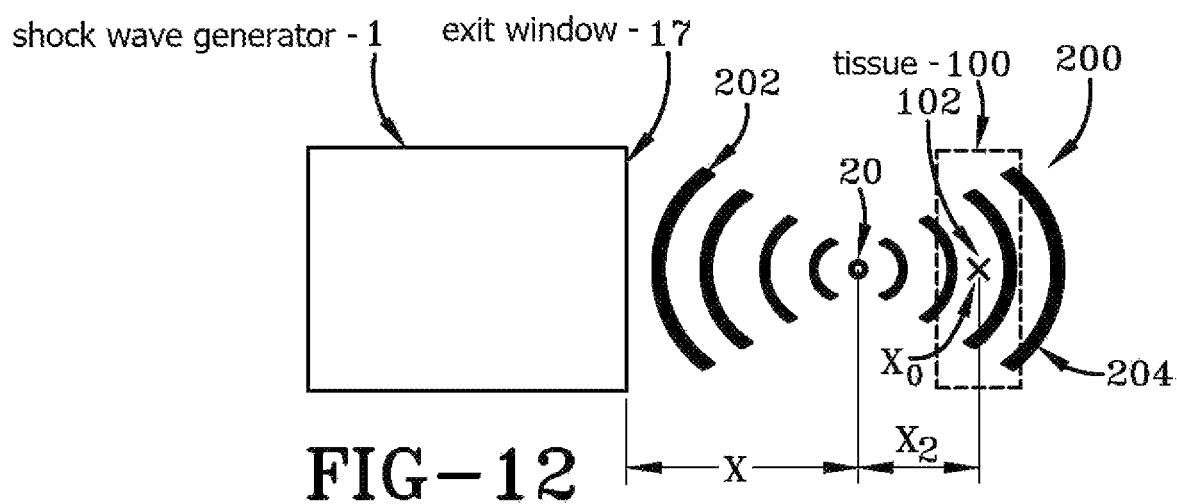
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. These FIGS. 10, 11 and 12 are particularly directed to destroying a mass like a tumor and provide a good example of how a focused wave could be used as an option to the unfocused wave if used at a low energy. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 a tissue 100 is shown generally centered on the focal point or volume 20 at a location $X_0$ within the tissue 100. In this orientation the emitted waves are focused and thus are emitting a high intensity acoustic energy at the location $X_0$. This location $X_0$ can be anywhere within or on the organ. Assuming the tissue 100 is a brain tissue having a tumorous mass 102 at location $X_0$ then the focus is located directly on the mass 102. In one method of treating an infection or mass 102 these focused waves can be directed to destroy or otherwise reduce the mass 102 by weakening the outer barrier shield of the mass 102.

With reference to FIG. 11, the tissue 100 is shifted a distance X toward the generator or source 1. The tissue 100 at location $X_0$ being positioned a distance $X-X_1$ from the source 1. This insures the tissue 100 is impinged by converging waves 202 but removed from the focal point 20. When the tissue 100 is tissue this bombardment of converging waves 202 stimulates the cells activating the desired healing response as previously discussed.

With reference to FIG. 12, the tissue 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the tissue 100 which when the tissue is a cellular tissue stimulates the cells to produce the desired healing effect or response.

Figure 13:
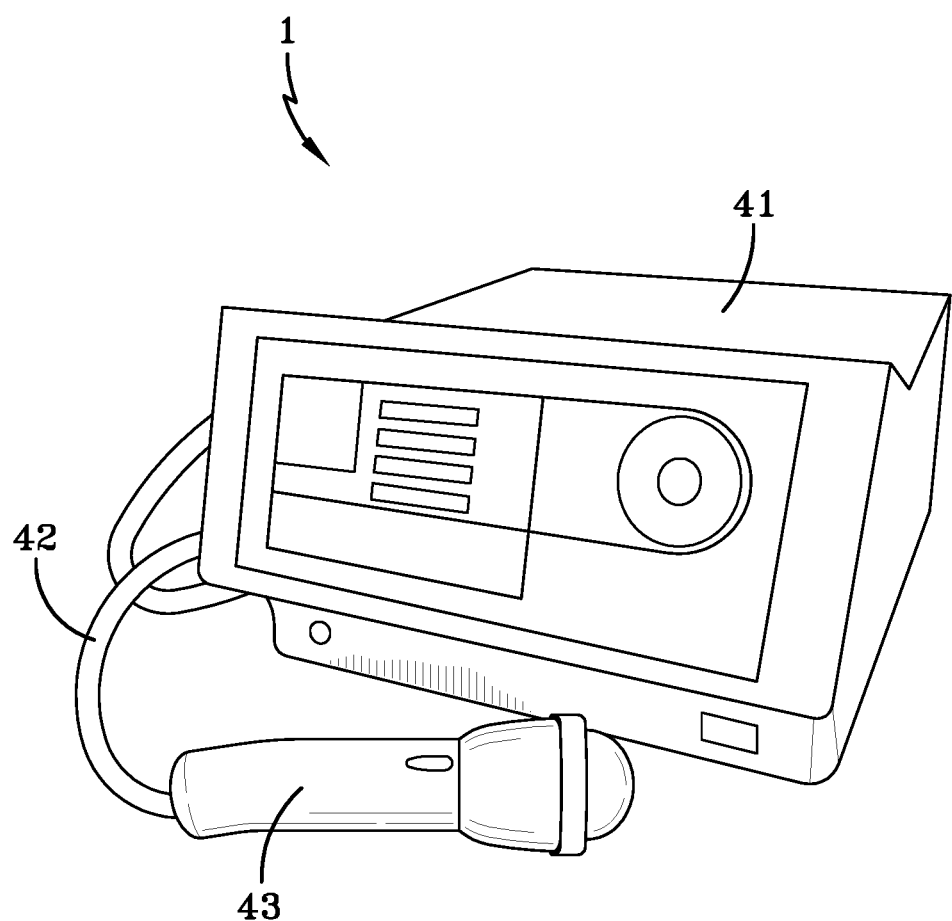
FIG. 13 shows a shock wave generator device.

FIG. 13 shows an exemplary shock wave device generator or source 1 with a control and power supply 41 connected to a hand-held applicator shock wave head 43 via a flexible hose 42 with fluid conduits. The illustrated shock wave applicator 43 has a flexible membrane at an end of the applicator 43 which transmits the acoustic waves when coupled to the skin by using a fluid or acoustic gel. As shown, this type of applicator 43 has a hydraulic spark generator using either focused or unfocused shock waves, preferably in a low energy level, less than the range of 0.01 mJ/mm2 to 0.3 mJ/mm$^2$. The flexible hose 42 is connected to a fluid supply that fills the applicator 43 and expands the flexible membrane when filled. Alternatively, a ballistic, piezoelectric or spherical acoustic shock wave device can be used to generate the desired waves.

Figure 14:
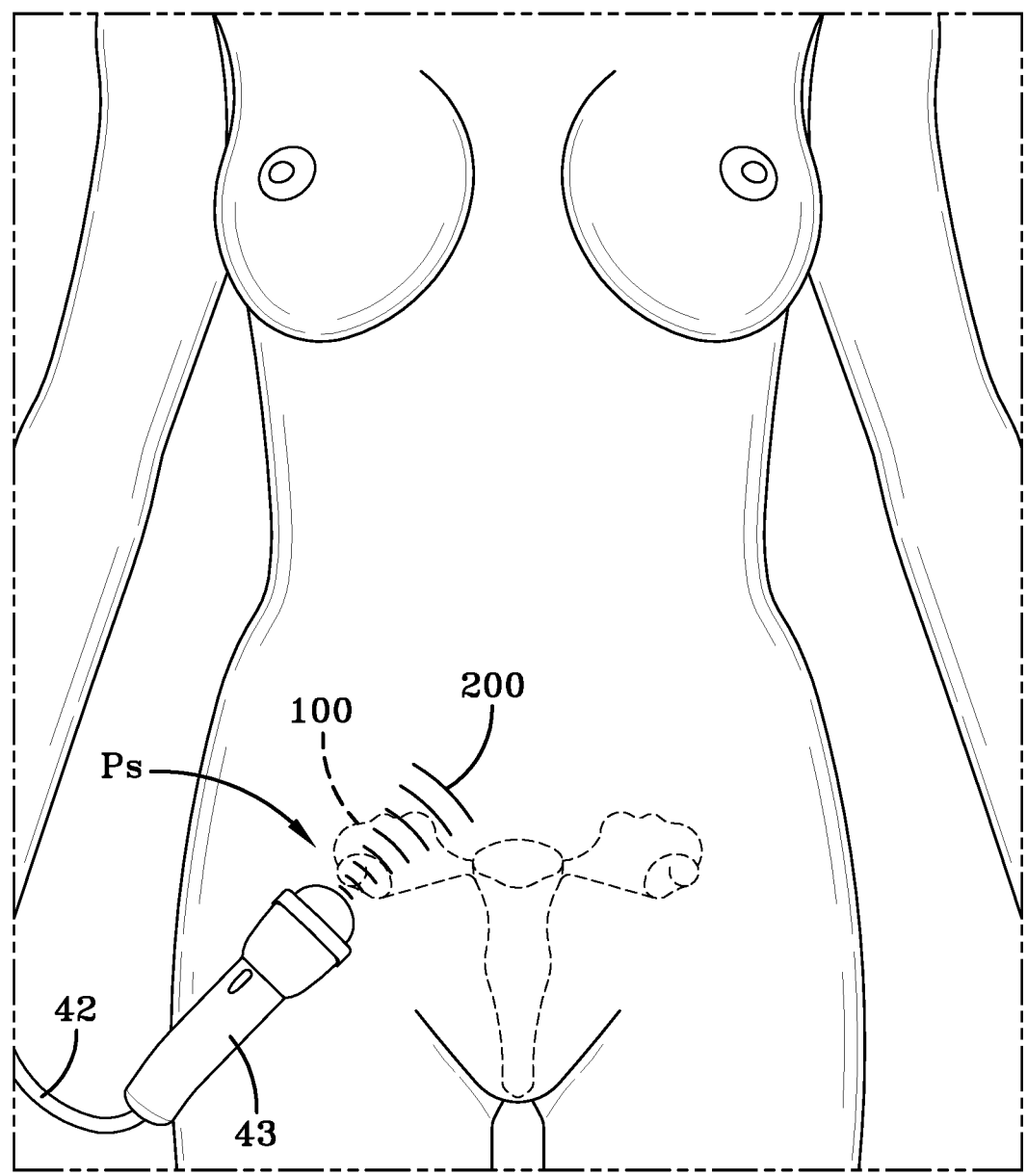
FIG. 14 shows the shock wave generator device directed at the ovaries of a female patient.

FIG. 14 is a perspective view of a portion of a female patient whose gland 100, in this case the ovaries 100, are being treated. A shock wave applicator head 43 is brought into contact with the skin $P_s$ preferably an acoustic gel is used to enhance the transmission of the shock waves 200 through the skin $P_s$ down to the glands 100, in this case the ovaries. The shock wave applicator head 43 can be hand held and manipulated across the skin $P_s$ to drive the shock waves 200 in the direction the shock wave head 43 is pointed to activate a stimulating response in the gland 100. The acoustic shock waves activate a cellular response within the treatment site. This response or stimulation causes an increase of nitric oxide and a release of a variety of growth factors such as VEGF. As shown, the flexible membrane is protruding outward and the applicator 43 has been filled with fluid, the transmission or emission of acoustic shock waves 200 is directed towards the ovaries 100. In order to accomplish a good transmission, it is important the flexible membrane be pressed against the patient's skin $P_s$ and as indicated coupling gels may be used. The ovaries 100 are on each side of the uterus just below the opening of the fallopian tubes that expend from the uterus to near the ovaries. By transmitting the shock waves 200 to the ovaries 100 is it believed that a modulation of the secretions from the ovaries can be made. This modulation or adjustment is achieved by transmitting the acoustic waves 200 at low energy directly onto the ovaries 100. As a result, in the event of low estrogen or progesterone, these secretions will be increased after treatment. Equally importantly, should there be an overabundance of estrogen or progesterone being emitted from the ovaries this can be reduced as the ovaries will be intelligently modulated in such a fashion that they will adjust the secretion level to achieve a more normal level of these secretions. It is important to note that the levels of estrogen and progesterone are controlled by certain hormones made in the pituitary gland. It is important that these levels be maintained within normal levels to be sure the female patient to be effectively be able to function in a normal and acceptable fashion for her health benefit. It is believed that a single treatment of the ovaries will achieve the desired modulation. However, repeated treatments may be administered to help maintain and control this secretion level of these hormones. Having achieved a schedule pattern of treatments is it possible to achieve regulation of this gland without the use of drugs or other stimulants.

Figure 15:
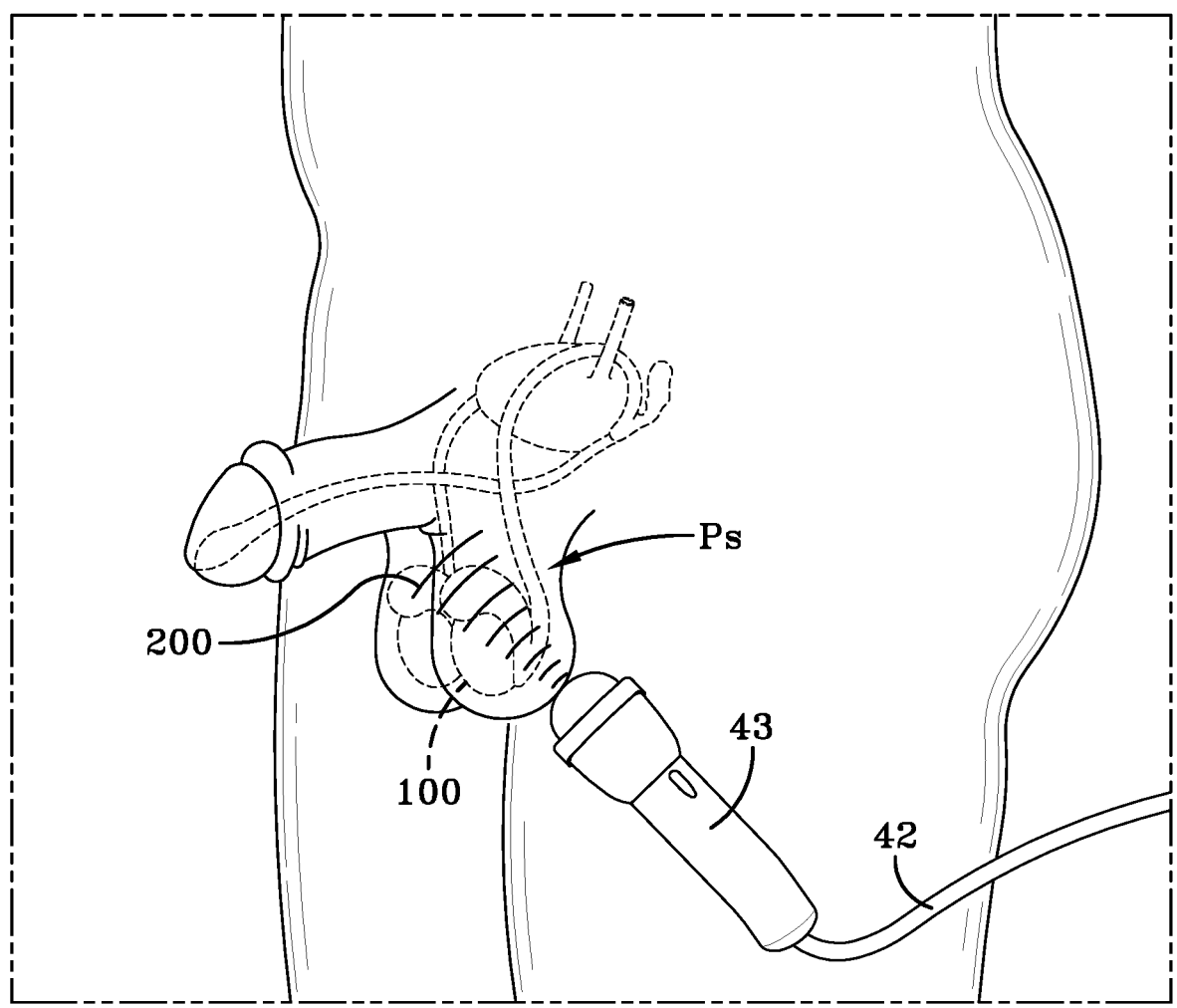
FIG. 15 shows the shock wave generator device directed at the testicles of a male patient.

With reference to FIG. 15, a partial view of a male patient whose gland 100, in this case the testicles 100, are being treated with acoustic shock waves 200. In this illustration, it is important to note that the applicator 43 presses against the skin $P_s$ of the scrotum and against the testicles 100. Preferably pressing the scrotum tightly against the testicles in such a fashion that the sac of the scrotum can be directed tightly against the applicator head membrane and the testicles themselves can be slightly compressed as the shock waves 200 are being transmitted directly towards the testicle 100. Both testicles, preferably are treated, and when doing so, it has been determined that an increase in secretion of hormones such as testosterone can occur. This is particularly useful in male patients where low levels of testosterone are being exhibited. Alternatively, if high levels of testosterone are being exhibited, the use of acoustic shock waves can intelligently modulate the amount of secretions. By applying a treatment of acoustic shock waves 200 to the testicles 100 that are secreting too much hormones or testosterone, a reduction of this level of secretion can occur. This adjustment feature is extremely valuable. In many cases an increase in testosterone is a desired result, however, in cases of male patients where too much testosterone is being produced, the use of the applicator directing acoustic shock waves has a modulating effect that helps to control the amount of secretions that are released from the testicles 100 to the patient. Again, this level of hormone control is achieved without the use of drugs or other chemicals and therefore can achieve beneficial results for the patient. A side effect of the treatment of acoustic shock waves 200 directly on the testicles 100 has been that a noticeable increase in the size of the testicles 100 occurs after treatment. Additionally, the ability of the male patient with low testosterone has been exhibited to overcome many of the attributes of erectile dysfunction. After these treatments, the shaft of the penis is actually increased in size as well as the ability of the patient to extend or increase his activity level when it comes to sexual arousal and sexual performance. It is important to note that the present inventors had directed a patent towards female and male reproductive systems, in males in particular for erectile dysfunction. It is also important to note that in this case, the treatment is directed at the testicle and thereafter the testicles are controlling or modulating the amount of hormone secretions. This is unique from what was previously done when there was an attempt to solve erectile dysfunction problems or impotency in male patients where the treatment was done on the genitalia, in particular the shaft area, and the testicles were in fact avoided as they were considered too sensitive an area to be directly treated with acoustic shock waves. It has been determined that this in fact was short sighted and that the treatment of the testicles alone can achieve the desired results and can achieve them in such a way that the energy levels are such that patient can do this without anesthesia and limited amount of discomfort during the treatment process. This is particularly unexpected in that the testicle areas are extremely sensitive and, in the past, has been considered an area to be avoided.

Figure 16:
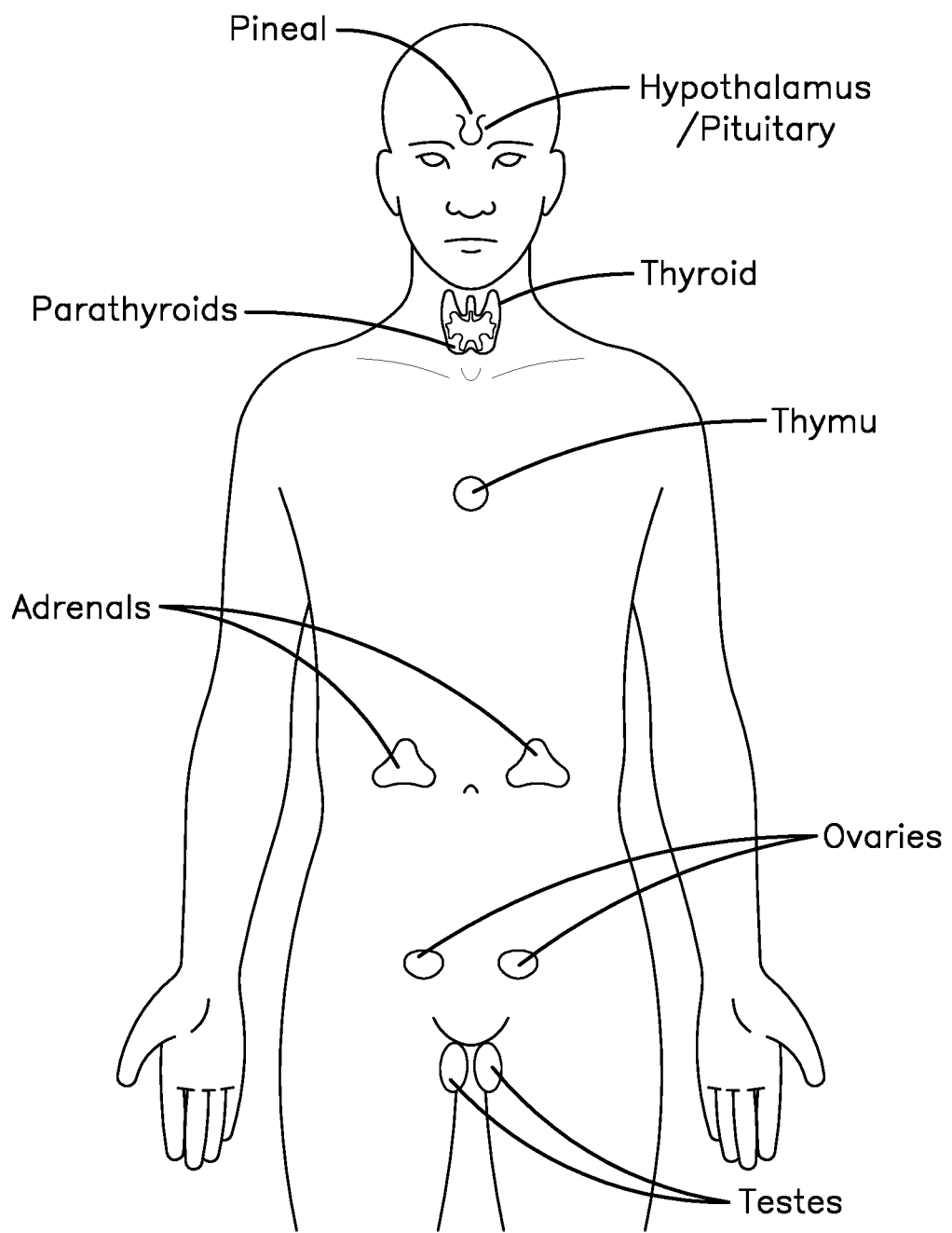
FIG. 16 shows a schematic view of a male/female showing general locations of glands in the human body.

With reference to FIG. 16, a general schematic view is shown of a male or female showing the general location of the various glands. As noted in FIG. 16, the pituitary gland controls many of these functions. It has been determined that the use of acoustic shock waves should be at the location where the hormone secretions are actually occurring. Which often is far removed from the pituitary gland. A general treatment of the pituitary gland may in fact be beneficial, however, it does not specifically isolate a particular gland for a particular function. The present invention has found that when treating particular functions, it is best to treat at the location where the secretions occur.

In addition to the fact that acoustic shock waves at low energy whether focused or unfocused can achieve the desired control of hormone secretions, it has also been determined that it will increase certain releases of growth factors and other activities such as the stimulation of cells within the region and additionally increased vascularization occurs in these regions where treatments have occurred. These and other benefits are provided in the invention as claimed herein.

The transmission of the shock waves 200 is preferred of a low energy density of 0.2 mJ/mm² whether using focused or unfocused shock waves. The acoustic shock waves pulse rapidly through the cells penetrating the cell membrane extremely rapidly due to the rapid rise to peak time and pass through exiting slower due to the slower return from peak amplitude. This asymmetric wave pattern rapidly compresses each cell on entry and slow decompresses the cell as it exits. This effective squeezing of each cell is believed to cause the release of growth factors such as VEGF and others and also creates nitric oxide, all beneficial to new blood vessel formation. This occurs as a transmission across the cell membranes without rupturing the native cells.

Furthermore, such acoustic shock wave forms can be used in combination with drugs, chemical treatments, irradiation therapy or even physical therapy and when so combined the stimulated cells will more rapidly assist the body's natural healing response and thus overcomes the otherwise potentially tissue damaging effects of these complimentary procedures.

The present invention provides an apparatus for an effective treatment of indications, which benefit from high or low energy pressure pulse/shock waves having focused or unfocused, nearly plane, convergent or even divergent characteristics. With an unfocused wave having nearly plane, plane, convergent wave characteristic or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm² or even as low as 0.000 001 mJ/mm². In a preferred embodiment, those low end values range between 0.1-0.001 mJ/mm². With these low energy densities, side effects are reduced and the dose application is much more uniform. Additionally, the possibility of harming surface tissue is reduced when using an apparatus of the present invention that generates unfocused waves having planar, nearly plane, convergent or divergent characteristics and larger transmission areas compared to apparatuses using a focused shock wave source that need to be moved around to cover the affected area. The apparatus of the present invention also may allow the user to make more precise energy density adjustments than an apparatus generating only focused shock waves, which is generally limited in terms of lowering the energy output. Nevertheless, in some cases the first use of a high energy focused shock wave targeting a treatment zone may be the best approach followed by a transmission of lower energy unfocused wave patterns.

It will be appreciated that the apparatuses and processes of the present invention can have a variety of embodiments, only a few of which are disclosed herein. It will be apparent to the artisan that other embodiments exist and do not depart from the spirit of the invention. Thus, the described embodiments are illustrative and should not be construed as restrictive.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method of modulating glandular secretions by administering acoustic shock waves to a gland of a patient, the gland is one of an ovary, a pituitary gland, an adrenal gland, a thyroid gland, a thymus, a pineal gland, a parathyroid, and a hypothalamus, the method comprises the steps of:
    activating an acoustic shock wave generator to emit acoustic shock waves;
    subjecting the gland to the acoustic shock waves to stimulate the gland to have a modulated response, wherein the modulated response is one of an adjustment in glandular secretions of hormonal release from the gland which increases low level hormonal output in the gland where the secretions are low relative to a normal level, or which decreases high level hormonal output in the gland where the secretions are high relative to a normal level, to stabilize erratic hormonal output in the gland to achieve the normal level of the glandular secretions; and
    wherein the emitted acoustic shock waves are low energy soft waves, the soft waves being focused or unfocused acoustic shock waves having an energy density of less than 0.4 mJ/mm$^2$, wherein the shock waves comprise amplitude above 0.1 MPa and rise times of the amplitude are below 100 nano-seconds with a duration of the acoustic shock waves being below 3 micro-seconds for a positive part of a cycle.

2. The method of claim 1, wherein the shock wave generator is acoustically coupled to the patient's skin using a coupling gel or liquid.

3. The method of claim 1, further comprising the step of stimulating the gland with a sufficient amount of acoustic shock waves to cause a release of nitric oxide.

4. The method of claim 3, further comprising the step of stimulating the gland with a sufficient amount of acoustic shock waves to cause a release of growth factors including Vascular Endothelial Growth Factor (VEGF).

5. The method of claim 4, further comprising the step of stimulating the gland with a sufficient amount of acoustic shock waves to cause new blood vessels to be created increasing vascularization.

6. The method of claim 1, is repeated one or more times.

7. The method of claim 1, wherein the low energy soft waves have the energy density in the range of 0.01 mJ/mm$^2$ to 0.4 mJ/mm$^2$.

8. The method of claim 7, wherein the low energy soft waves have the energy density in the range of 0.04 mJ/mm$^2$ to 0.3 mJ/mm$^2$.

9. The method of claim 1, wherein the gland receives between 100 and 2000 acoustic shock waves per therapy session.

10. The method of claim 1, wherein the gland is an ovary.

11. The method of claim 10, wherein the modulated response is an increase in a hormonal release of estrogen wherein a patient was exhibiting low levels of estrogen relative to a normal level of estrogen.

12. The method of claim 10, wherein the modulated response is a decrease in a hormonal release of estrogen wherein a patient was exhibiting high levels of estrogen relative to a normal level of estrogen.

13. The method of claim 1, wherein the modulated response reduces panic attacks and anxiety by decreasing levels of adrenaline by the adrenal gland.

14. A method of modulating glandular secretions by administering acoustic shock waves to a testicle of a patient to decrease a level of testosterone within the patient, comprises the steps of:
    activating an acoustic shock wave generator to emit acoustic shock waves;
    subjecting the gland to acoustic shock waves to stimulate the testicle to have a modulated response wherein the modulated response is an adjustment in glandular secretions of testosterone from the testicle which decreases high level testosterone output in the testicle to stabilize erratic hormonal output in the testicle where the secretions are high relative to a normal level to achieve the normal level of testosterone secretions; and
    wherein the emitted acoustic shock waves are low energy soft waves, the soft waves being focused or unfocused acoustic shock waves having an energy density of less than 0.4 mJ/mm$^2$, wherein the shock waves comprise amplitude above 0.1 MPa and rise times of the amplitude are below 100 nano-seconds with a duration of the acoustic shock waves being below 3 micro-seconds for a positive part of a cycle.

* * * * *